US009291547B2

(12) United States Patent
Liu et al.

(10) Patent No.: US 9,291,547 B2
(45) Date of Patent: Mar. 22, 2016

(54) IMMERSION REFRACTOMETER (75) Inventors: Ai Qun Liu, Singapore (SG); Lip Ket Chin, Singapore (SG)

(73) Assignee: Nanyang Technological University, Singapore (SG)

( * ) Notice: Subject to any disclaimer, the term of this patent is extended or adjusted under 35 U.S.C. 154(b) by 327 days.

(21) Appl. No.: 13/549,169

(22) Filed: Jul. 13, 2012

(65) Prior Publication Data
US 2013/0016341 A1 Jan. 17, 2013

Related U.S. Application Data (60) Provisional application No. 61/508,218, filed on Jul. 15, 2011.

(51) Int. Cl.
| G01N 21/03 | (2006.01) |
| G01N 21/05 | (2006.01) |
| B01L 3/00 | (2006.01) |
| G01N 21/41 | (2006.01) |

(52) U.S. Cl.
CPC ............... *G01N 21/05* (2013.01); *G01N 21/41* (2013.01); *B01L 3/5027* (2013.01); *G01N 2021/0325* (2013.01); *G01N 2021/0346* (2013.01); *G01N 2021/058* (2013.01)

(58) Field of Classification Search
CPC ........... C12Q 1/6816; C12Q 2565/629; C12Q 1/6834; B82Y 30/00; C12N 13/00
USPC .......................................................... 356/128
See application file for complete search history.

(56) References Cited

U.S. PATENT DOCUMENTS

| 6,170,981 | B1 * | 1/2001 | Regnier | B01F 5/0645 366/336 |
| 7,294,503 | B2 * | 11/2007 | Quake | B01L 3/502784 204/604 |
| 7,344,681 | B1 * | 3/2008 | Fiechtner | B01F 13/0093 366/DIG. 1 |
| 7,691,244 | B2 * | 4/2010 | Levitan | B01F 13/0076 204/450 |
| 7,718,420 | B2 * | 5/2010 | Kim | B01F 5/0641 435/287.3 |
| 8,134,705 | B2 * | 3/2012 | Kaduchak et al. | 356/337 |
| 8,292,492 | B2 * | 10/2012 | Ho | B01D 65/08 366/336 |
| 8,309,408 | B2 * | 11/2012 | Ward | G01N 15/1404 210/748.01 |
| 2003/0175947 | A1 * | 9/2003 | Liu | B01F 11/0071 435/288.5 |
| 2003/0198130 | A1 * | 10/2003 | Karp | B01D 17/00 366/341 |

(Continued)

OTHER PUBLICATIONS

Droplet-based microfluidic system for multicellular tumor spheroid formation and anticancer drug testing Yu et al, Royal Society of Chemistry, Lab Chip, 2010, 10, pp. 2424-2432.*

(Continued)

*Primary Examiner* — Tri Ton
*Assistant Examiner* — Jarreas C Underwood
(74) *Attorney, Agent, or Firm* — Seed IP Law Group PLLC (57) ABSTRACT An immersion refractometer includes a microchamber having an inlet and an outlet for allowing a sample containing microorganism particles to flow therethrough, wherein the microchamber comprises at least one trapping site for trapping a microorganism particle in each respective trapping site, and a micromixer for mixing a plurality of liquids to form an external medium, wherein the micromixer and the microchamber are in fluid communication to introduce the external medium into the microchamber. Use of the present immersion refractometer in a method of identifying microorganism particles contained in a sample is also provided.

14 Claims, 11 Drawing Sheets

(56) References Cited

U.S. PATENT DOCUMENTS

2008/0277387 A1* 11/2008 Landers ............... H05B 6/80
   219/687
2010/0099076 A1* 4/2010 Mao ................ G01N 33/54313
   435/5

OTHER PUBLICATIONS

Adam, "The *Giardia lamblia* genome," *International J. Parasitology* 30:475-484, 2000.

Barer et al., "Refractometry of living cells," *Nature* 171:710-724, Apr. 25, 1953.

Barer, "Refractometry and Interferometry of Living Cells," *J. Optical Society of America* 47(6):545-556, Jun. 1957.

Campbell et al., "Viability of *Cryptosporidium parvum* Oocysts: Correlation of in Vitro Excystation with Inclusion of Exclusion of Fluorogenic Vital Dyes," *Appl. & Environ. Microbiology* 58(11):3488-3493, Nov. 1992.

Chin et al., "Differential single living cell refractometry using grating resonant cavity with optical trap," *Appl. Phys. Lett.* 91:243901, 2007, 4 Pages.

Chin et al., "An optofluidic volume refractometric using Fabry-Perót resonator with tunable liquid microlenses," Biomicrofluidics 4:024107, 2010, 7 Pages.

Chin et al., "Protozoon classifications based on size, shape and refractive index using on-chip immersion refractometer," *Transducers* '11, Jun. 5-9, 2011, Beijing, China, 4 Pages.

Chin et al., "Null-method in immersion refractometry for biophysical measurement of *Cryptosporidium* and *Giardia lamblia*," *15th International Conference on Miniaturized Systems for Chemistry and Life Sciences*, Oct. 2-6, 2011, Seattle, Washington, USA, 3 Pages.

Current et al., "Cryptosporidiosis," *Clinical Microbiology Reviews* 4(3):325-358, Jul. 1991.

De Vos et al., "Silicon-on-Insulator microring resonator for sensitive and label-free biosensing," *Optics Express* 15:7610-7615, Jun. 11, 2007.

Di Carlo et al., "Single-Cell Enzyme Concentrations, Kinetics, and Inhibition Analysis Using High-Density Hydrodynamic Cell Isolation Arrays," *Anal. Chem.* 78(14):4925-4930, Jul. 15, 2006.

DiGiorgio et al., "Cryptosporidium and Giardia Recoveries in Natural Waters by Using Environmental Protection Agency Method 1623," *Appl. & Environ. Microbiology* 68(12):5952-5955, Dec. 2002.

Fayer et al., "Effects of Low Temperatures on Viability of *Cryptosporidium parvum* Oocysts," *Appl. & Environ. Microbiology* 62(4):1431-1433, Apr. 1996.

Gradus et al., "Water Quality and Waterborne Protozoa," *Clinical Microbiology Newsletter* 11(6):121-125, Aug. 15, 1989.

Harris et al., "*Cryptosporidium parvum*: Structural components of the oocyst wall," *J. Parasitol.* 85(5):839-849, 1999.

Leach et al., "The detection and determination of ethyl and methyl alcohols in mixtures by the immersion refractometer," *J. American Chemical Society* 27:964-972, 1905.

Marshall et al., "Waterborne Protozoan Pathogens," *Clin. Microbiol. Rev.* 10(1):67-85; 404, Jan. 1997.

Mengeaud et al., "Mixing Processes in a Zigzag Microchannel: Finite Element Stimulations and Optical Study," *Anal. Chem.* 74(16):4279-4286, Aug. 15, 2002.

Minkovich et al., "Holy fiber tapers with resonance transmission for high-resolution refractive index sensing," *Optics Express* 13(19):7609-7614, Sep. 19, 2005.

Monzón-Hernández et al., "High-resolution refractive index sensing by means of a multiple-peak surface Plasmon resonance optical fiber sensor," *Sensors and Actuators B* 115:227-231, 2006.

Peeters et al., "Effect of Disinfection of Drinking Water with Ozone or Chlorine Dioxide on Survival of *Cryptosporidium parvum* Oocysts," *Appl. & Environ. Microbiology* 55(6):1519-1522, Jun. 1989.

Rose, "Occurrence and Significance of *Cryptosporidium* in Water," *J. American Water Works Assoc.* 80:53, 1988.

Schroeder et al., "A fibre Bragg grating refractometer," *Measurement Sci. & Technol.* 12:757-764, 2001.

Stein, "The great Sydney water crisis of 1998," *Water, Air & Soil Pollution* 123:419-436, 2000, 19 Pages.

Steiner et al., "Protozoal Agents: What are the Dangers for the Public Water Supply?," *Annu. Rev. Med.* 48:329-340, 1997.

Stirling et al., "Waterborne cryptosporidiosis outbreak, North Battleford, Saskatchewan, spring 2001," *Canada Communicable Disease Report* 27(22):185-192, Nov. 15, 2001.

Zhang et al., "High urea and NaCl carbonylate proteins in renal cells in culture and in vivo, and high urea causes 8-oxoguanine lesions in their DNA," *PNAS* 101(25):9491-9496, Jun. 22, 2004.

* cited by examiner

FIGURE 11 ical Patent Application No. 61/508,218...

IMMERSION REFRACTOMETER

CROSS-REFERENCE TO RELATED APPLICATION

This application claims the benefit of priority of U.S. Provisional Patent Application No. 61/508,218, filed 15 Jul. 2011, the contents of which being hereby incorporated by reference in its entirety for all purposes.

TECHNICAL FIELD

The invention relates to an immersion refractometer, and in particular, to an on-chip immersion refractometer for use in identifying microorganism particles in water.

BACKGROUND

In recent years, water safety has gained more attention as water is one important resource and may cause fatal outbreak especially in densely-populated city if health-affecting contaminants are present in treated water. One of the main sources of contaminants in water resource is protozoan parasites, which include, for example, *Entamoeba histolytica, Cryptosporidium parvum* (*C. parvum*), *Cyclospora cayetanensis*, and *Giardia lamblia* (*G. lamblia*). These protozoan parasites are normally transmitted through the oral-fecal route and can cause acute short-term infection to the host such as diarrhea and abdominal pain. However, the infection is severe and also fatal for kids, elderly and immune-compromised individuals such as HIV positive patients.

Among these, *C. parvum* and *G. lamblia* are two commonly found waterborne protozoan parasites. *C. parvum* exists in the spore phase outside the host, which is encapsulated within a hard cyst. An infection of cryptosporidiosis can be initiated with as few as 10 oocysts. In 2001, an outbreak occurred in Saskatchewan of Canada had reported about 6,000 cases of cryptosporidiosis. The source of contamination is the drinking water, which shows that it is vital to ensure the absence of *C. parvum* oocyst in drinking water. Similar to *C. parvum* oocysts, *G. lamblia* exists also in cyst outside the host, which is resistant to conventional treatment techniques such as chlorination and ozonolysis. In 1998, *G. lamblia* outbreak was reported in Sydney, Australia due to the mismeasurement of the concentrations of microbes in the water supply. Therefore, it is essential to monitor the concentration of *C. parvum* oocysts and *G. lamblia* cysts in treated water.

Current widely accepted monitoring protocol employed for *C. parvum* and *G. lamblia* identification is the USEPA Method 1623. The protocol incorporates the collection of 10 L water sample, sample filtration, immunomagnetic separation, and immune-fluorescence assay microscopy. However, the processing time of the current protocol requires more than 6 hours and the protocol is not applicable for on-site monitoring due to the dependence of laboratory facilities such as fluorescence staining.

Therefore, there remains a need to provide for an improved identification method to overcome, or at least alleviates, the above problems.

SUMMARY

According to one aspect of the invention, there is provided an on-chip immersion refractometer. The design of the on-chip immersion refractometer consists of two key features, namely, a trapping microchamber and an integrated micromixer.

In various embodiments, the immersion refractometer includes a microchamber. The microchamber may have an inlet and an outlet for allowing a sample containing microorganism particles to flow therethrough. The microchamber may further include at least one trapping site for trapping a microorganism particle in each respective trapping site. The immersion refractometer further includes a micromixer for mixing a plurality of liquids to form an external medium. The micromixer and the microchamber are in fluid communication such that the external medium may be introduced into the microchamber.

According to another aspect of this disclosure, there is provided a method of identifying microorganism particles contained in a sample.

In various embodiments, the method includes introducing the sample into a microchamber of an immersion refractometer of the previous aspect, mixing a plurality of liquids in a micromixer of the immersion refractometer to form an external medium, introducing the external medium into the microchamber, varying the refractive index of the external medium to determine the refractive index of the microorganism particles, determining the size and shape of the microorganism particles, and comparing the determined refractive index, size and shape of the microorganism particles with known database to identify the microorganism particles.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

FIG. 9*a-b* show the pixel intensity analysis of *G. lamblia* cyst when the external medium is tuned to the refractive index of 1.3326, 1.4324 and 1.4631, respectively. The *G. lamblia* cyst appears to be invisible when the refractive index of the external medium is 1.4324.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural changes may be made without departing from the scope of the invention. The various embodiments are not necessarily mutually exclusive, as some embodiments can be combined with one or more other embodiments to form new embodiments.

Since microorganisms such as protozoan parasites commonly found in treated water supply are limited in species, large in size (several to tens μm), regular in shape (cyst), resistant to chemical treatment, it may be feasible to identify different protozoa based on their morphologies (size and shape) and biophysical properties (refractive index). In one embodiment, the size and the shape of the protozoan parasites may be determined by a microscopic imaging system.

Refractive index of a biological sample is correlated with the mass density of its internal constituents such as protein concentration, nucleus contents and cellular sub-organelles. In protozoan parasites, the contents inside the cysts for different species are distinctive. For example, *C. parvum* ocysts contain up to 4 sporozoites, which are bow-shaped and *G. lamblia* cysts contain 4 nuclei, clearly visible axostyles and lack of mitochondria. Based on these differences, their refractive index values are different. Thus, refractive index may be a distinctive parameter for different protozoan species.

An approach to verify the possibilities of using the above three parameters for protozoa identification is to build up a database of these three parameters based on different protozoan species.

Thus, in one aspect of this disclosure, an on-chip immersion refractometer is provided. In another aspect, a method of identifying microorganism particles contained in a sample using the immersion refractometer is provided.

In order to collect multiple measurement results per sample run, the immersion refractometer may be designed to include an array of trapping sites to enable, for example, 50 or more microorganism particles to be trapped simultaneously for measurement. The size and the shape may be measured by capturing a high-resolution microscopic image. The refractive indices of the microorganism particles may be measured by the null method of phase-contrast imaging via immersion refractometry (Barer R., *J Optical Soc. America* (1957), 47:545).

Immersion refractometry refers to the measurement of refractive index of a sample by immersing it into a liquid and observing the optical properties of light passing through the substance and the liquid. In various embodiments, a null-method is employed on the phase-contrast microphoto to determine the refractive index of the sample as shown in FIG. 1*a-c*. When a sample is immersed into a medium with refractive index lower than the one of the sample (FIG. 1*a*), the light passing through the sample is experiencing phase delay as compared to the one passing through the medium. The phase delay experienced by the light can be expressed as Eq. (1):

$$\Delta\Phi=(n_{cyst}-n_{medium})t_{cyst} \quad (1)$$

where $t_{cyst}$ is the thickness of the sample, $n_{cyst}$ and $n_{medium}$ are the refractive indices of the sample and the medium, respectively. However, in bright-field microscopy, the brightness contrast associated with the phase delay experienced is limited. Therefore, phase-contrast microscopy is employed to enhance the brightness contrast caused by the phase delay experienced. By observing the phase-contrast microphoto, the sample appears brighter than the medium. By slowly increasing the refractive index of the medium, the brightness difference is reduced; and at one point, the sample appears to be invisible in the medium as shown in FIG. 1*b*. The refractive indices of the sample and medium match equally at this instance. Subsequently, when the refractive index of the medium is further increased, the light passing through the medium is experiencing phase delay as compared to the one passing through the sample. By observing the phase-contrast microphoto, the sample appears brighter than the medium (FIG. 1*c*). Therefore, in the experiments, the samples are exposed to external medium varying from low to high refractive index. At the instance when the samples become invisible, the refractive index of the sample is obtained by measuring the refractive index of the respective medium.

The sensitivity of the system depends on two criteria: (1) the phase shift detection limit of the phase-contrast microscopy, and (2) the resolution of the liquid refractometer used to measure the refractive index of the medium. For phase-contrast microscopy, the phase shift detection limit is smaller than λ/100. Therefore, the refractive index resolution is represented by Eq. (2):

$$\Delta n=\frac{\lambda}{100t_{cyst}} \quad (2)$$

where λ is the wavelength of the light source. From Eq. (2), it can be concluded that the refractive index resolution is higher for thicker sample. The phase shift detection limit of the phase-contrast microscopy depends on the light absorption of the phase plate, in which λ/1000 can be achieved with heavily absorbing phase plates. The resolution of the phase-contrast microscopy with limit of λ/100 and λ/1000 for a 5 μm sample are approximately $10^{-3}$ and $10^{-4}$, respectively. Once a sample-matched immersion medium has been found, the refractive index of the medium is measured. Several volumetric refractometers, which have been widely reported with excellent refractive index resolution ($<10^{-4}$) can be employed. In the experiments, a handheld refractometer (PAL-RI, Atago) with a resolution of $10^{-4}$ is used, such that it is not the limiting factor in the measurement.

In various embodiments, the immersion refractometer 10 includes a microchamber 12 as shown in FIG. 2*a*. The microchamber 12 may be configured to allow the sample 18 containing microorganism particles 20 to flow therethrough. Thus, the microchamber 12 may have an inlet 14 for the introduction of a sample 18 into the microchamber 12 and an outlet 16 for the exit of the sample 18 from the microchamber 12.

The sample 18 may contain microorganism particles 20. The sample may be any fluid that is to be investigated for the presence (or absence) of microorganism particles. For example, the sample may be treated water or untreated water, blood, or urine. Exemplary microorganisms may include water-borne parasites such as *Entamoeba histolytica*, *Cryptosporidium parvum* (*C. parvum*), *Cyclospora cayetanensis*, and *Giardia lamblia* (*G. lamblia*).

As mentioned above, the size and the shape of the microorganism particles may be determined by a microscopic imaging system. Typical particle size of various microorganisms ranges from 1 to 50 μm, such as 1 to 40 μm, 1 to 30 μm, 1 to 20 μm, or 1 to 10 μm.

Thus, in various embodiments, the microstructures formed in the immersion refractometer 10 may be as small as about 1 to 2 um, depending on the constraints of current fabrication techniques.

Typical microorganism particle shape may be classified based on ovality (O) defined by Eq. (3):

$$O = \frac{D-d}{D} \quad (3)$$

where D and d are the major and minor diameters of the microorganism particle, respectively. In theory, for spherical particles, the ovality is 0 while for oval particles, the ovality is less than 1. However, for practical purposes it is common to define an ovality of 0.3 or more for an oval microorganism particle and an ovality of less than 0.3 for a spherical microorganism particle.

In the illustrations given in the following paragraphs, it has been determined that the major and minor diameters of *C. parvum* oocysts range from about 3 to 7 μm, respectively, and *C. parvum* oocysts are generally spherical in shape based on the measured ovality of less than 0.3 with a mean of 0.13. On the other hand, the major and minor diameters of *G. lamblia* cysts are measured to be ranging from about 8 to 14 μm and 3 to 8 μm, respectively, and *G. lamblia* cysts are generally oval in shape based on measured ovality of more than 0.3 with a mean of 0.48. Thus, different microorganisms can be differentiated from one another based on at least the size and shape of the respective particle.

In various embodiments, the microchamber 12 may further include at least one trapping site 22 for trapping a microorganism particle 20 in each respective trapping site 22. In certain embodiments, the microchamber 12 consists of multiple single particle trapping sites 22, in which the microorganism particles 20 flowing through the microchamber 12 can be trapped in the respective site individually.

Two exemplary designs of the trapping sites 22 have been employed herein to illustrate the concept of trapping particles of a certain size. FIG. 2b shows a single layer trapping site 22 for trapping particles with a size larger than 8 μm, for example. The single layer trapping site 22 shown in FIG. 2b has a V-shape cross-section which decreases in size in the direction of the sample flow. By restricting the width of the lower gap to 8 μm (assuming that this is the particle size of interest, e.g. cysts), particles with a size larger than 8 μm flowing through the microchamber 12 can be trapped in the gap of the trapping site 22. Once the particle 20 is trapped, the sample flow is blocked and deviated to avoid other particles from being trapped in the same trapping site 22 already occupied. Due to constraints of current fabrication techniques, it may be difficult to fabricate a gap smaller than 5 μm (assuming that this is another particle size of interest, e.g. oocysts) to trap the smaller particles 20. To overcome this limitation, a double layer trapping site 22 is introduced (as such described e.g. in Di Carlo et al., *Analytical Chemistry* (2006), 78:4925). The double layer structure consists of a top layer (for example, height of 20 μm) and a bottom layer, wherein the top layer and the bottom layer are configured to form a gap of, for example, 2 μm between the top layer and the bottom layer. Smaller particles such as oocyst can then be effectively trapped by the smaller gap when the sample flows through the microchamber 12 (FIG. 2c). The thickness of the photoresist to control the vertical gap or the height of the microstructure may range from about 1 to 250 μm.

In various embodiments, the microchamber 12 may include a plurality of trapping sites. In yet various embodiments, the microchamber 12 may include a plurality of single layer trapping sites 22 and a plurality of double layer trapping sites 22. It is to be understood and appreciated by the skilled person that other configurations of the trapping site 22 are also possible, so long as each trapping site 22 is able to trap a respective single microorganism particle therein.

Figure 2:
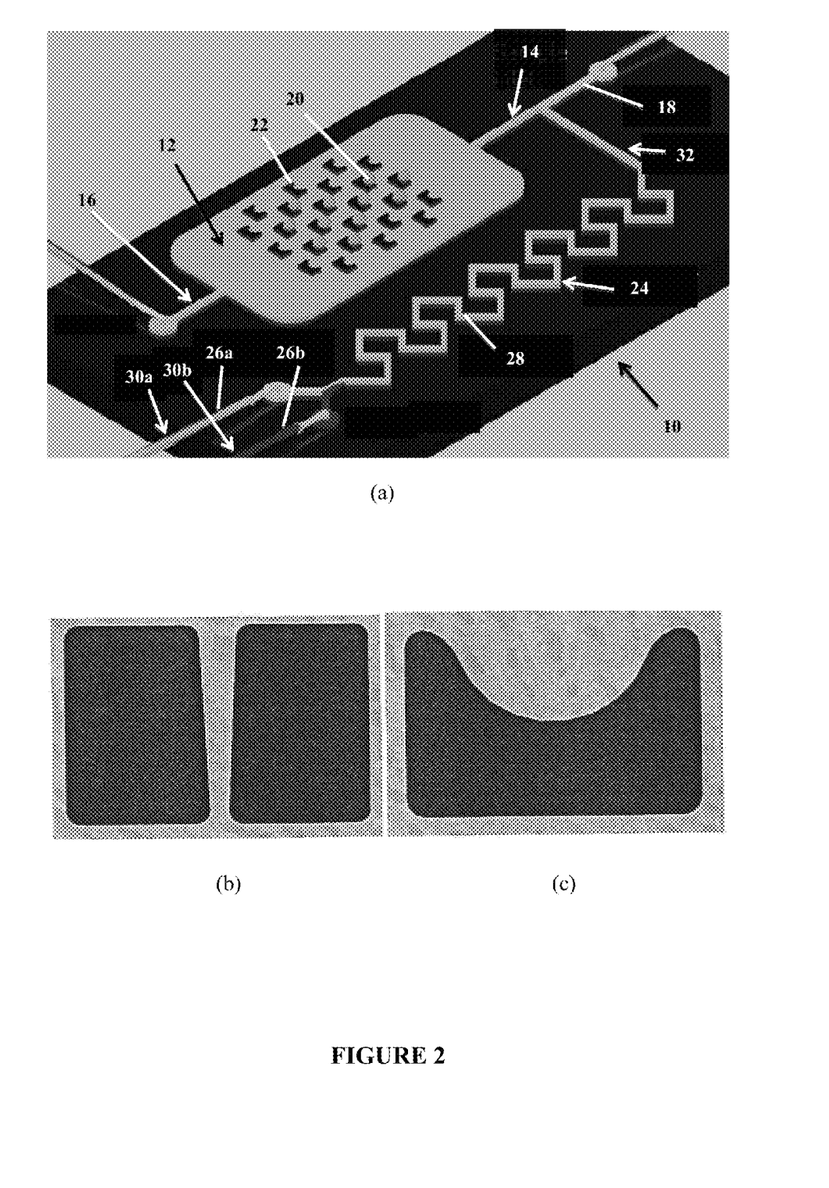
FIG. 2 shows schematic illustrations of (a) the on-chip immersion refractometer in accordance with one aspect of this disclosure, (b) the single layer trapping site, and (c) the double layer trapping site.

In various embodiments, the immersion refractometer 10 may further include a micromixer 24 for mixing a plurality of liquids 26a, 26b to form an external medium 28. The micromixer 24 may include a plurality of inlets 30a, 30b for introducing the plurality of liquids 26a, 26b into the micromixer 24. The micromixer 24 and the microchamber 12 are in fluid communication such that the external medium 28 may be introduced into the microchamber 12. In one embodiment, the fluid communication may be provided by including in the micromixer 24 an outlet 32 in fluid connection with the inlet 14 of the microchamber 12 as shown in FIG. 2. In alternative embodiments, the micromixer 24 may include an outlet 32 directly connected to the microchamber 12 to introduce the external medium 28 therein.

To perform on-site immersion refractometry as discussed above, the micromixer 24 is integrated with the immersion refractometer 10. A plurality of liquids 26a, 26b, for example, 2, 3, or 4 different liquids are introduced into the micromixer 24 and then mixed together to form the external medium 28. The liquids 26a, 26b are selected such that they are miscible in each other to form a homogeneous solution of the external medium 28. Each of the liquid 26a, 26b has a respective refractive index different from each other. The refractive index of the external medium 28 is determined and may be varied by the respective refractive index of the plurality of liquids, the respective amount of each liquid 26a, 26b of the external medium 28, or the respective flow rate of each liquid 26a, 26b of the external medium 28.

In various embodiments, the refractive index of the external medium 28 is varied from low refractive index to high refractive index by controlling the respective flow rate of the liquids 26a, 26b introduced into the micromixer 24. Exemplary embodiments of two liquids 26a, 26b used herein are deionized (DI) water (n=1.3326) and 99% glycerol solution (n=1.4651). Therefore, the refractive index of the external medium 28 can be tuned from 1.3326 to 1.4651 by tuning the flow rate ratio between the two liquid flows.

Figure 3:
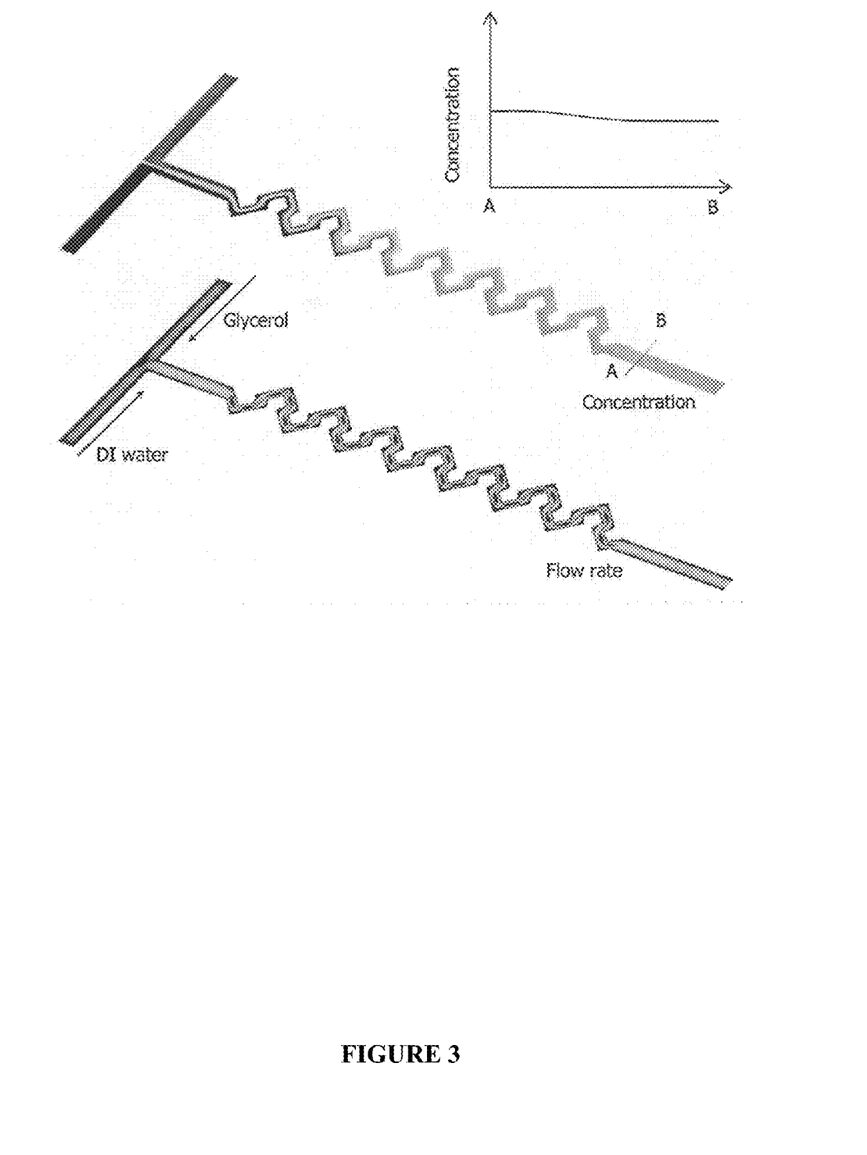
FIG. 3 shows a simulation of the integrated micromixer. The concentration uniformity along the cross-section is within 3%.
Figure 4:
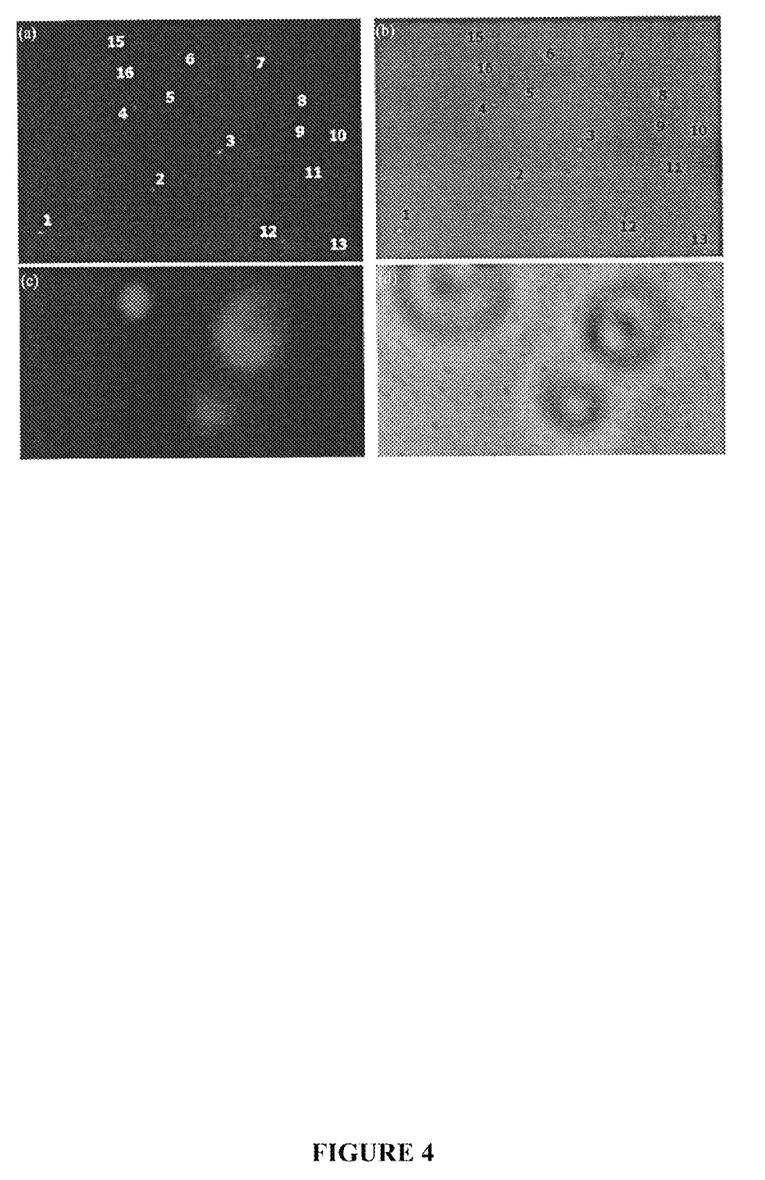
FIG. 4 shows (a) optical micrograph, (b) respective phase-contrast microphoto of slow-freezed *C. parvum* oocysts, (c) and (d) are the zoom view of the slow-freezed *C. parvum* oocysts.
Figure 5:
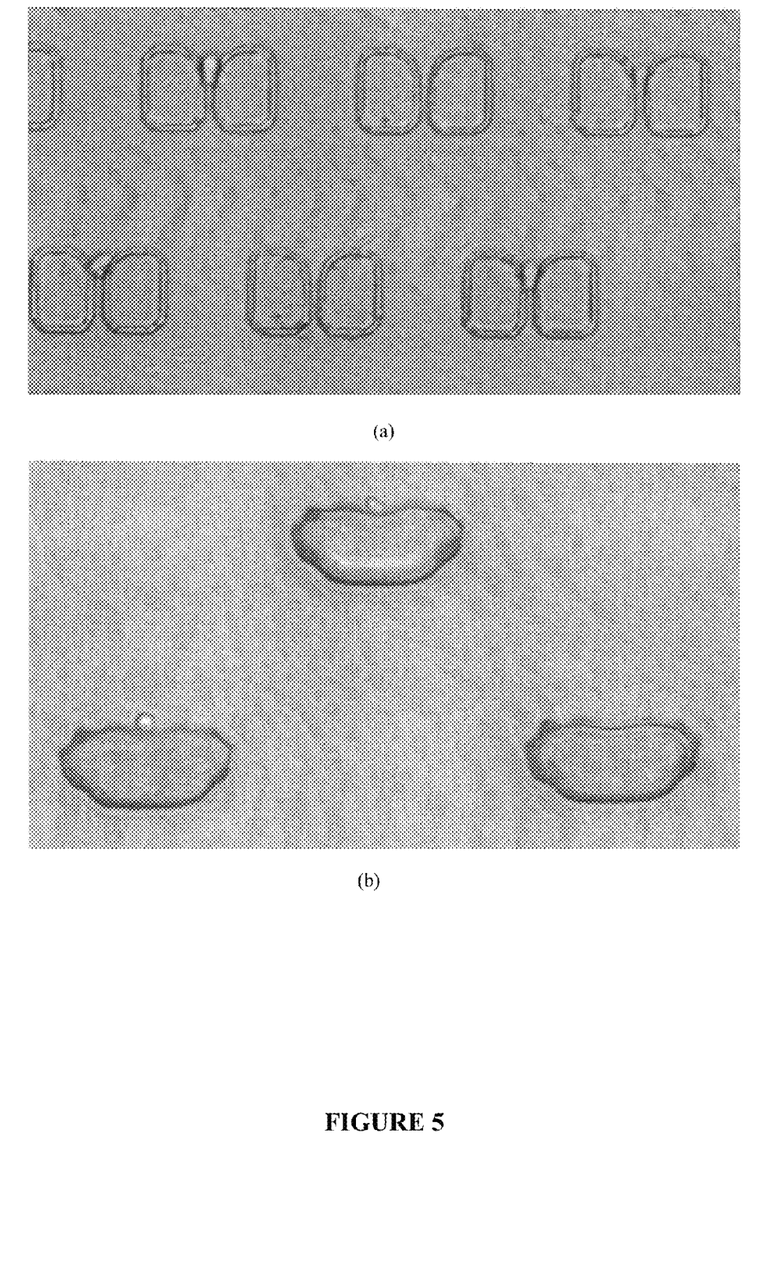
FIG. 5 show microphotos of (a) trapped *G. lamblia* cysts, and (b) trapped *C. parvum*.
Figure 6:
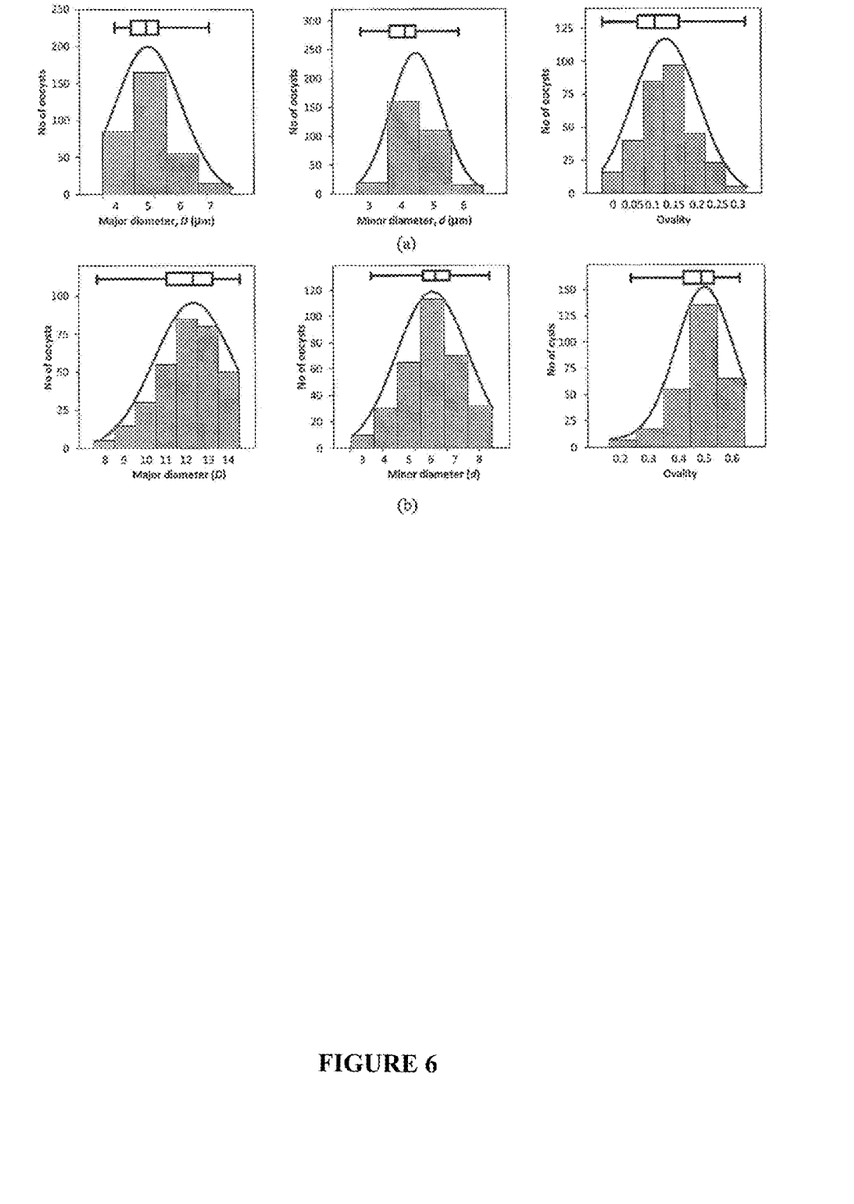
FIG. 6 show morphological measurements of (a) *C. parvum* oocysts, and (b) *G. lamblia* cysts. The sample size is 300. The major and the minor diameters are measured to the nearest μm.
Figure 7:
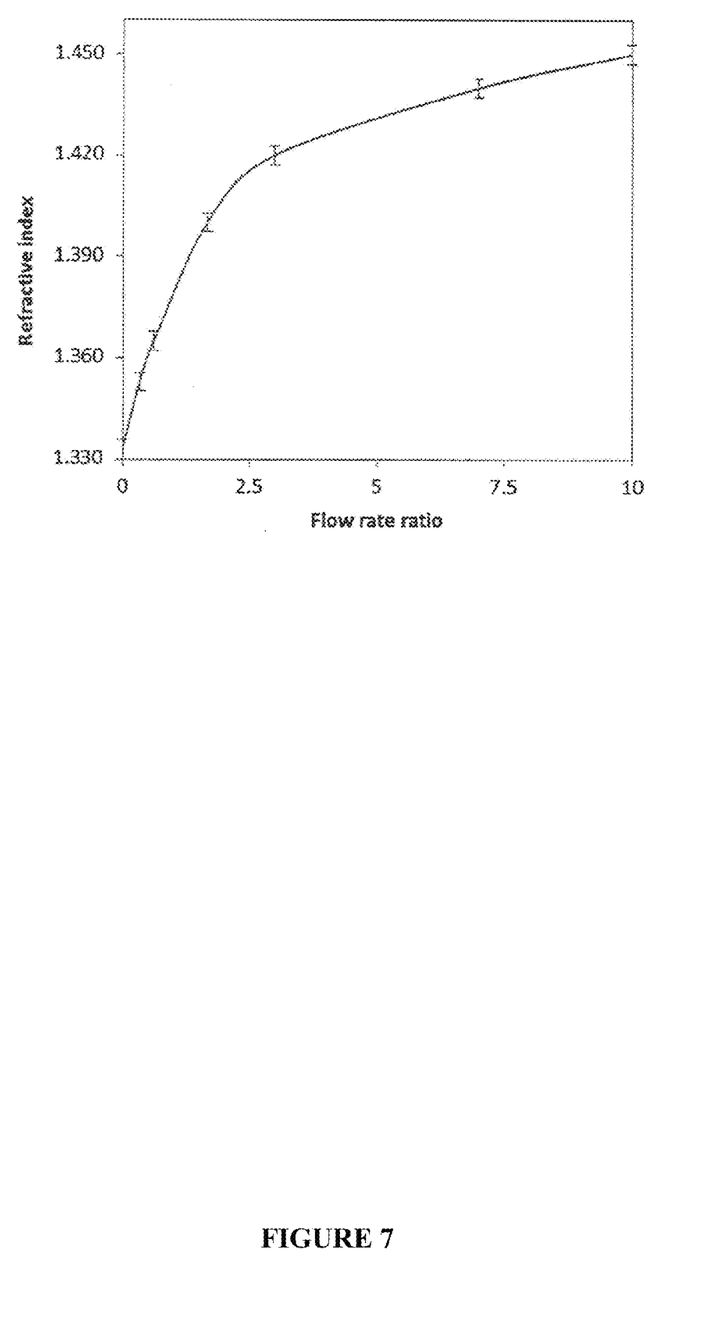
FIG. 7 shows the tuning of the refractive index of the external medium by varying the flow rate ratio between the DI water and the glycerol solution.
Figure 8:
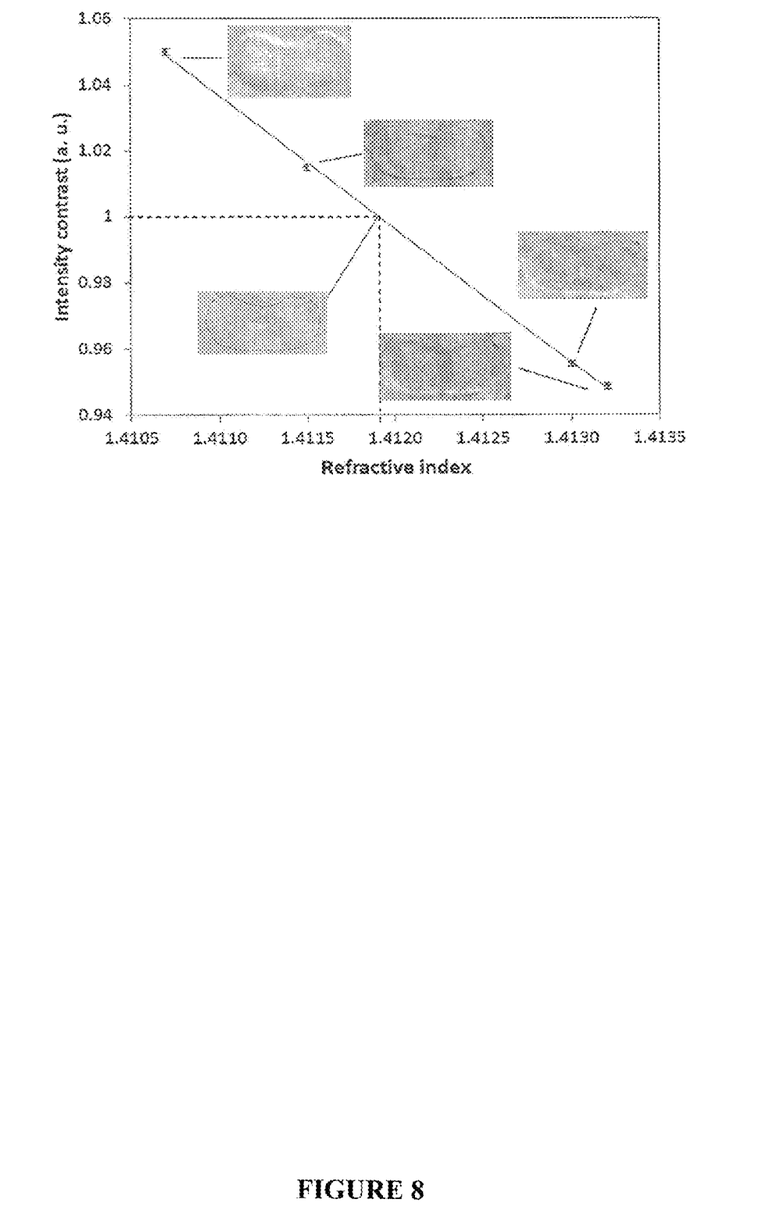
FIG. 8 shows the intensity contrast variation by tuning the refractive index of the external medium.
Figure 9:
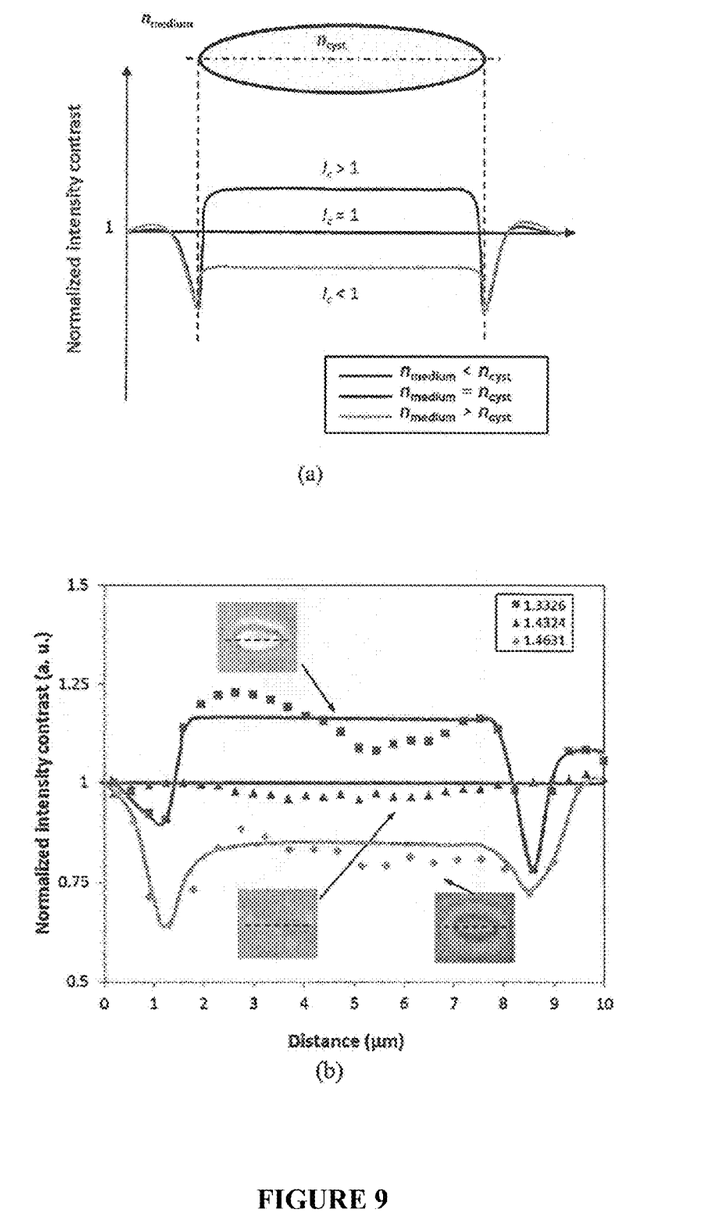
Figure 10:
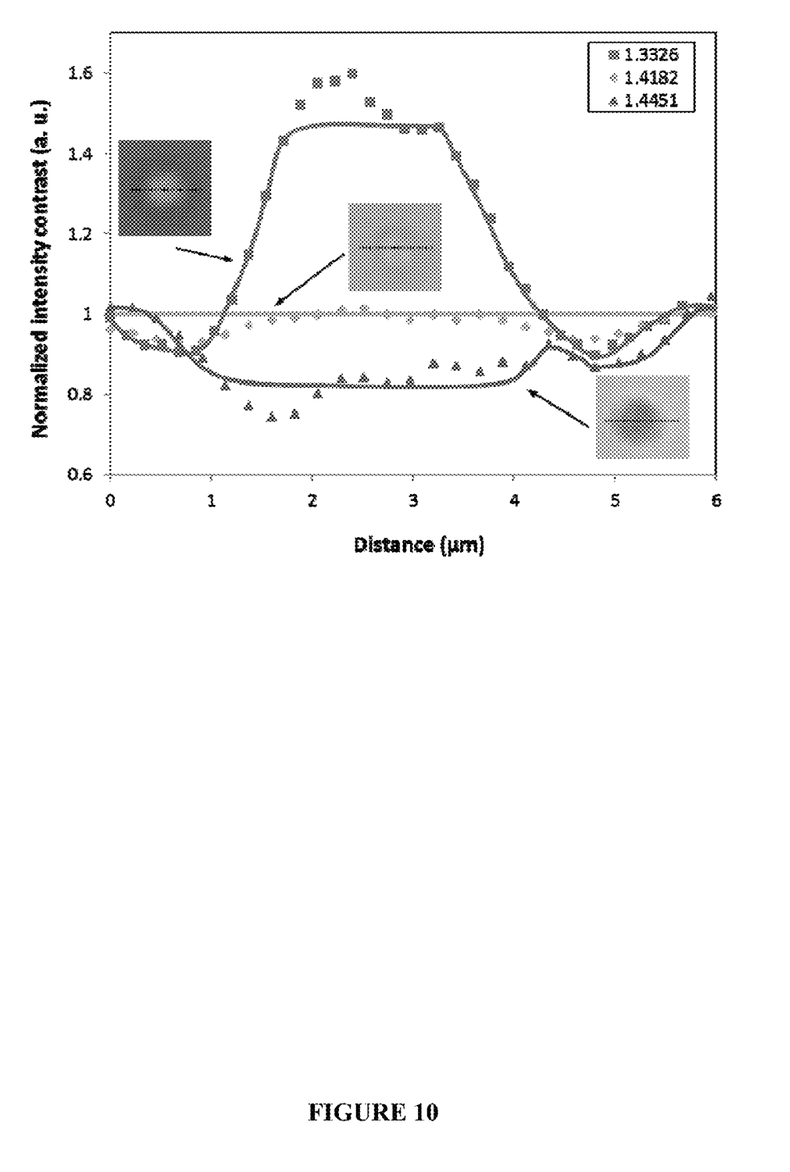
FIG. 10 shows the pixel intensity analysis of *C. parvum* oocyst when the external medium is tuned. The oocyst appears to be invisible when the refractive index of the external medium is 1.4182
Figure 11:
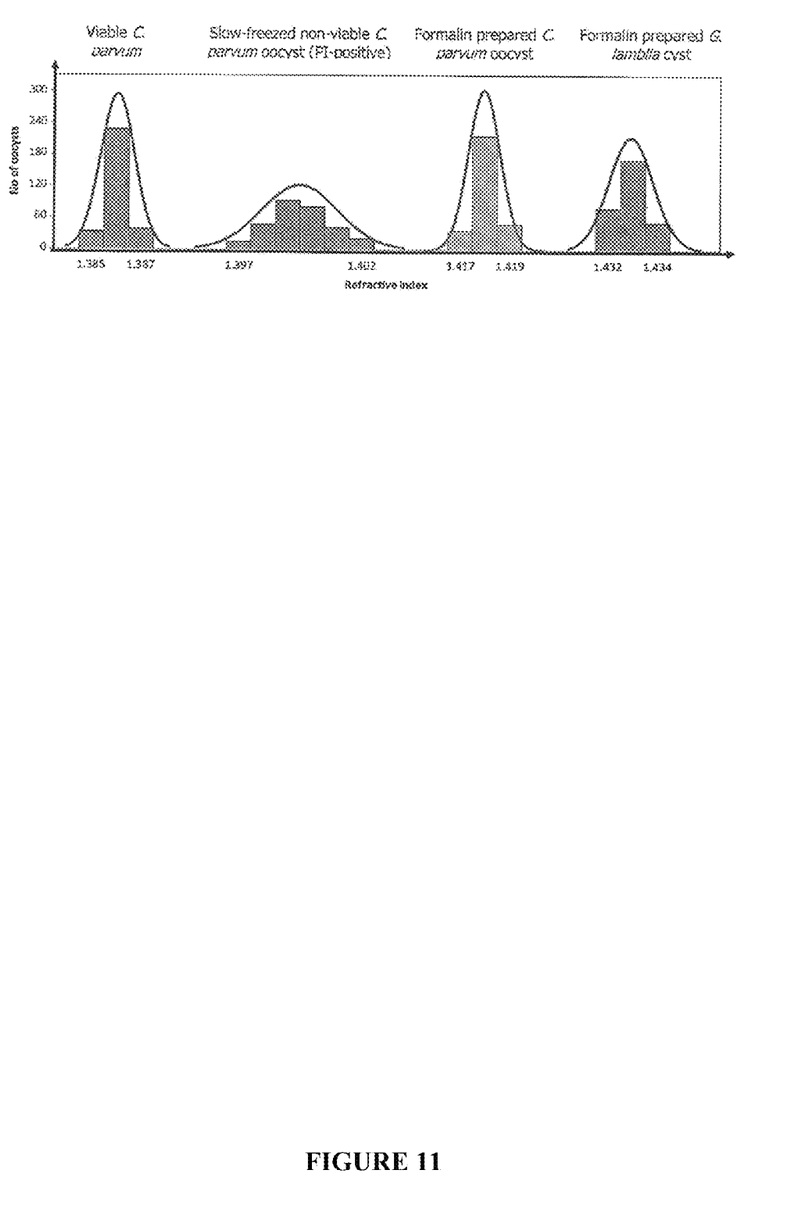
FIG. 11 shows the statistical results of the measured refractive index for 4 sample types: live *C. parvum* oocysts, slow freezed non-viable *C. parvum* oocysts, formalin prepared *C. parvum* oocysts, and formalin prepared *G. lamblia* cysts. The four sample types are differentiable at the resolution of $10^{-3}$ RIU.

In various embodiments, the micromixer 24 may be a microchannel. The microchannel may be formed of a linear or non-linear geometry. In the embodiment shown in FIG. 3, the integrated micromixer 24 is formed of a microchannel of a zigzag geometry (as such described e.g. in Mengeaud et al., *Analytical Chemistry* (2002), 74:4279). The concentration of the external medium 28 across the cross-section of the zigzag micromixer 24 is highly uniform with a variation of lower than 3%.

Figure 1:
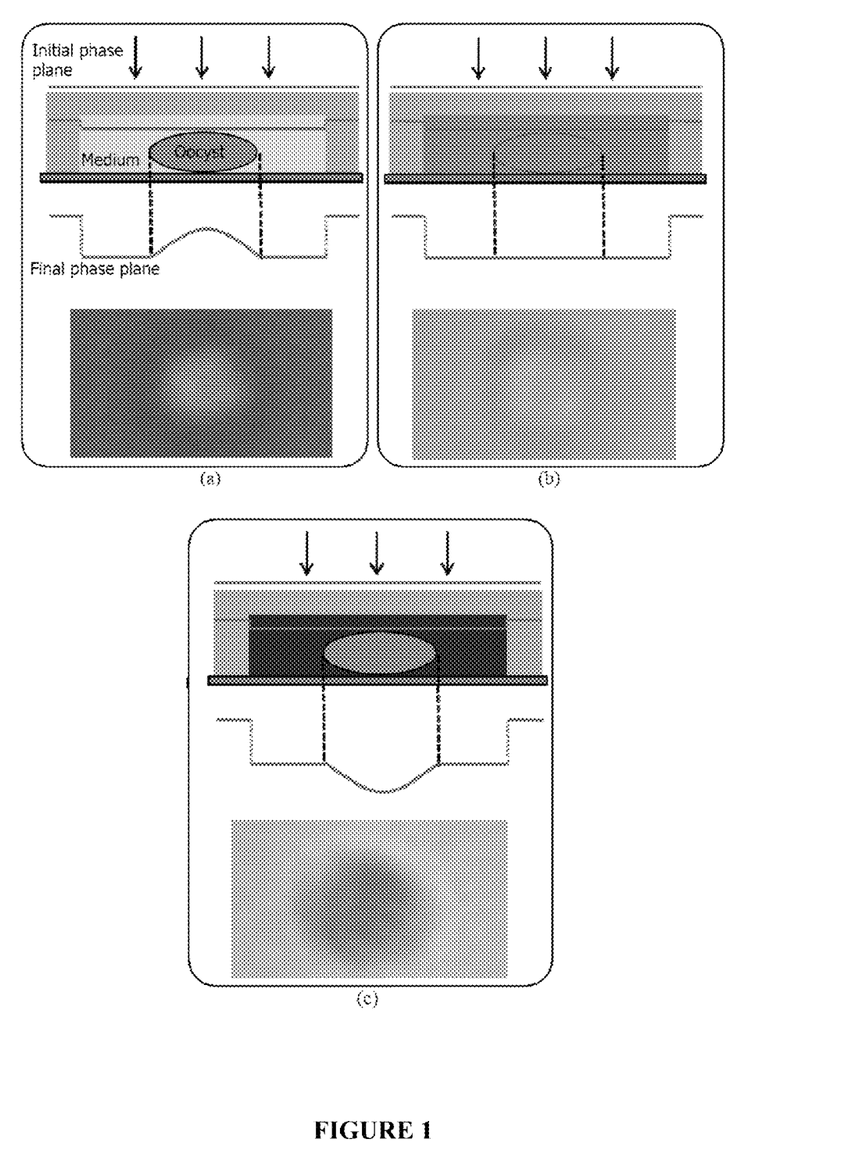
FIG. 1 illustrates the working principle of the null method in immersion refractometry: The phase transformation and the phase-contrast microphoto of the oocyst being immersed into a medium with refractive index (a) lower than, (b) same as, and (c) higher than the one of the oocyst.

As described above, the refractive index of the microorganism particles 20 trapped in the trapping sites 22 is determined by the varying the refractive index of the external medium 28 until the circumstance where the particles become invisible in the external medium 28 (i.e. FIG. 1b). At this instance when the boundary of the particles disappear into the external medium 28, i.e. become invisible, the refractive index of the external medium 28 matches that of the microorganism particles 20.

Based on the determined refractive index, size and shape of the microorganism particles 20, these parameters are then compared with known database to identify the microorganism particles 20.

In order that the invention may be readily understood and put into practical effect, particular embodiments will now be described by way of the following non-limiting examples.

EXAMPLES

An immersion refractometer developed based on Micro-Opto-Fluidic-System for the measurement of size, shape and refractive index of protozoa in treated water is described herein. The refractive indices of the samples are measured with high precision of less than $10^{-3}$. The measurements are focused on two protozoan species, i.e. *C. parvum* oocysts and *G. lamblia* cysts. In addition, the effect on the refractive index value by the viability of *C. parvum* oocyst is also investigated. With the developed on-chip immersion refractometer, the database of protozoa can be expanded to different protozoan species.

The microfluidic chip was fabricated in polydimethylsiloxane (PDMS) material using the standard soft lithography process. A SU8 photoresist layer with desired thickness (SU8-2 for 2 μm and SU8-10 for 20 μm) is spin-coated onto a silicon wafer (CEE 200, Brewer Science). The photoresist is developed after prebaking, UV exposure, and post baking. With the master developed, PDMS (sylgard-184, Dow Corning) mixture is poured over the master, degassed and baked for an hour at 75° C.

For single-layer PDMS structure, the patterned PDMS slab is then bonded to a PDMS-coated glass slide by exposing to air plasma using the corona treater (BD-25, Electro-Technic Products).

On the other hand, for double-layer PDMS structure, each PDMS slab is patterned by a layer of microstructures. Both PDMS slabs are aligned using a mask aligner and bonded together. In the experiments, the samples and the liquids are injected into the micromixer microchannel using syringe pumps (NE-I000, New Era). The phase-contrast microphotos are captured using cooled color digital CCD camera (Micropublisher 5.0, Qimaging) under the inverted research microscope (IX81, Olympus).

In the experiments, four different protozoa are prepared: (1) viable *C. parvum* oocysts, (2) slow-freezed non-viable *C. parvum* oocysts, (3) formalin prepared *C. parvum* oocysts, and (4) formalin prepared *G. lamblia* cysts. The viable *C. parvum* oocysts and the formalin prepared samples are obtained directly from Waterborne Inc. To inactivate the *C. parvum* oocysts, the oocysts are placed into a freezer with temperature set at −20° C. for 3 days. The assessment of oocyst viability is based on the inclusion of the fluorogenic vital dye, propidium iodide (PI), by the oocyst (P4170, Sigma-Aldrich). The oocysts suspended in 10% PBS solution are incubated with PI for 2 hours at 37° C. The oocysts are then washed with PBS solution to remove excess PI dissolved in the medium. For those non-viable oocysts, PI is diffused into them and can be detected by fluorescence microscopy (Excitation: 493 nm, Emission: 630 nm) as shown in FIG. 4. The fluorescent microphotos were captured using an inverted fluorescence microscope (IX81, Olympus) equipped with a cooled color CCD camera (DP-70, Olympus). Based on the microphotos, the major diameter, minor diameter and the ovality of the samples are measured.

For spherical sample, the ovality is 0; and for oval sample, the ovality is less than 1. For each group of protozoa, 300 samples were measured to obtain the average size, shape and refractive index.

All samples are suspended in tap water and injected into the microchannel. As the samples flowing into the trapping microchamber, they are trapped in the trapping sites as shown in FIG. 5*a-b*. For *G. lamblia* cysts, the single layer trapping site with a trapping gap of 8 μm is employed. The *G. lamblia* cysts are trapped within the gap as shown in FIG. 5*a*. On the other hand, for *C. parvum* oocysts, the double layer trapping site is employed as shown in FIG. 5*b*.

Once the trapping sites are filled with samples, the sizes and the ovalities of the samples are measured. FIG. 6*a-b* show the statistical results of *C. parvum* oocysts and *G. lamblia* cysts. For *C. parvum* oocysts, the major and minor diameters are ranging from 3 to 7 μm. The *C. parvum* oocysts are generally spherical in shape, such that the measured ovalities are lower than 0.3 and with a mean of 0.13. On the other hand, the major and minor diameters of *G. lamblia* cysts are measured to be ranging from 8 to 14 μm and 3 to 8 μm, respectively. Since *G. lamblia* cysts are generally oval in shape, their ovalities are higher than 0.3, with a mean value of 0.48.

For the measurement of the refractive index of the cysts, the external medium in the microchamber is varied by changing the flow rate ratio of the DI water and the glycerol solution. The refractive index of the external medium as a function of the flow rate ratio ($Q_{glycerol}/Q_{water}$) is illustrated in the graph of FIG. 7. When the microchannel is filled with DI water, the refractive index is 1.3326. Subsequently, the refractive index is increased at a rate of 0.029 RIU by increasing the flow rate of the glycerol inlet. At the point where the flow rate ratio is 2.5 and the refractive index of the external medium is 1.415, the increment rate is reduced to 0.004 RIU.

The on-chip immersion refractometry is characterized by observing the phase-contrast microphotos of a PDMS trapping site and tuning the external medium from 1.4107 to 1.4132. For each phase-contrast microphoto, the intensity contrasts are determined by dividing the average pixel intensity of the PDMS structure with the average pixel intensity of the external medium. The intensity contrast measured under different external medium is illustrated in FIG. 8. When the external medium has lower refractive index as compared to the one of PDMS, the PDMS structure appears to be brighter and protruding. On the other hand, when the external medium has higher refractive index as compared to the one of the PDMS, the PDMS structure appears to be darker and concave. The sensitivity of the technique is determined to be −41.67 per refractive index unit. Based on the interpolation of the measured data, the PDMS structure has a refractive index of 1.4119. It is confirmed by injecting external medium of the same refractive index and the PDMS structure has become invisible as shown in the inset of FIG. 8.

FIG. 9*a-b* show the pixel intensity analysis for formalin prepared *G. lamblia* cyst by varying the refractive index of the external medium. The intensity contrast is higher than 1 when the refractive index of the cyst is higher than the one of the external medium, and vice versa. The matching refractive index occurs when the intensity contrast is equal to 1. This occurs when the external medium has a refractive index of 1.4324. Therefore, the *G. lamblia* cyst is measured to have a refractive index of 1.4324. The process is repeated for formalin prepared *C. parvum* oocysts and the result is shown in FIG.

10. The matching refractive index is measured as 1.4182. Therefore, the *C. parvum* oocyst has a refractive index of 1.4182.

In addition to the above two samples, the developed on-chip immersion refractometer is employed to measure another two samples, i.e. viable and slow-freezed non-viable *C. parvum* oocysts. The statistical results are shown in FIG. 11. The sample size measured is about 300 cysts for each sample type. The results show that viable *C. parvum* oocysts have refractive index ranging between 1.385 and 1.387. For slow-freezed *C. parvum* oocysts, their non-viability is confirmed by the positive results of the PI viability tests. Their refractive index is measured to be ranging from 1.397 to 1.402. Subsequently, formalin prepared *C. parvum* oocysts and *G. lamblia* cysts have refractive index ranging from 1.417 to 1.419 and 1.432 to 1.434, respectively. It can be concluded that these four sample types can be easily differentiated based on their refractive index measured at least in the resolution of $10^{-3}$ RIU. Together with the parameters of size and shape, a protozoa database can be built up to provide an alternative technique for protozoa identification in treated water source.

In summary, an on-chip immersion refractometer is designed, fabricated and demonstrated. The refractometer has two key functions: (1) trapping of cysts (>50) in an array of trapping sites; and (2) tuning the refractive index of the external medium to perform the null-method phase-contrast imaging. The size, the shape and the refractive index of *C. parvum* oocysts and *G. lamblia* cysts were investigated using the on-chip immersion refractometer. The results show that *C. parvum* oocysts and *G. lamblia* cysts can be differentiated using these three parameters (*C. parvum* oocyst: size of 3 to 7 μm, spherical with ovality lower than 0.3, and refractive index of 1.418; *G. lamblia* cyst: size of 8 to 12 μm, oval with ovality higher than 0.3, and refractive index of 1.433). In addition, the viability of *C. parvum* oocysts can be differentiated as well based on the refractive index value (viable: 1.386; non-viable: 1.400). The results show that it is feasible to use these three parameters for the identification of the protozoan species. The database may be expanded to other kinds of protozoan species to obtain the full spectra of the protozoan species based on these three parameters.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. An immersion refractometer comprising:

a microchamber having an inlet and an outlet for allowing a sample containing microorganism particles to flow therethrough, wherein the microchamber comprises at least one trapping site for trapping a microorganism particle in each respective trapping site; and a micromixer for mixing a plurality of liquids to form an external medium, wherein the micromixer and the microchamber are in direct fluid connection to introduce the external medium into the microchamber for immersing the trapped microorganism particle in the external medium.

2. The immersion refractometer of claim 1, wherein the micromixer comprises a plurality of inlets for introducing the plurality of liquids into the micromixer.

3. The immersion refractometer of claim 1, wherein the micromixer comprises an outlet in fluid connection with the inlet of the microchamber.

4. The immersion refractometer of claim 3, wherein the micromixer is a microchannel formed of a non-linear geometry.

5. The immersion refractometer of claim 4, wherein the microchannel has a zigzag geometry.

6. The immersion refractometer of claim 1, wherein the microchamber comprises a plurality of trapping sites.

7. The immersion refractometer of claim 1, wherein each trapping site has a V-shaped cross-section, the cross-section decreases in size in the direction of the sample flow.

8. The immersion refractometer of claim 1, wherein each trapping site has a double layer structure consisting of a top layer and a bottom layer, wherein the top layer and the bottom layer are configured to form a gap between the top layer and the bottom layer.

9. A method of identifying microorganism particles contained in a sample, comprising:

introducing the sample into a microchamber of an immersion refractometer, wherein the immersion refractometer comprises:

a microchamber having an inlet and an outlet for allowing a sample containing microorganism particles to flow therethrough, wherein the microchamber comprises at least one trapping site for trapping a microorganism particle in each respective trapping site; and a micromixer for mixing a plurality of liquids to form an external medium, wherein the micromixer and the microchamber are in fluid communication to introduce the external medium into the microchamber;

mixing a plurality of liquids in the micromixer of the immersion refractometer to form the external medium;

introducing the external medium into the microchamber;

varying the refractive index of the external medium to determine the refractive index of the microorganism particles;

determining the size and shape of the microorganism particles; and comparing the determined refractive index, size and shape of the microorganism particles with known database to identify the microorganism particles.

10. The method of claim 9, wherein varying the refractive index of the external medium comprises varying the respective amount of each liquid of the external medium.

11. The method of claim 9, wherein varying the refractive index of the external medium comprises varying the respective flow rate of each liquid introduced into the micromixer.

12. The method of claim 9, wherein determining the refractive index of the microorganism particles comprises determining the refractive index of the external medium corresponding to the situation whereby the microorganism particles become invisible in the external medium.

13. The method of claim 9, wherein determining the size of the microorganism particles comprises determining the major diameter (D) and the minor diameter (d) of the microorganism particles.

14. The method of claim 13, wherein determining the shape of the microorganism particles comprises determining the ovality (O) of the microorganism particles, wherein ovality (O) is defined by Eq. (3):

$$O = \frac{D-d}{D}. \tag{3}$$

* * * * *